US011045633B2

(12) United States Patent
Harrison et al.

(10) Patent No.: US 11,045,633 B2
(45) Date of Patent: Jun. 29, 2021

(54) CANNULA FOR CONNECTING MEDICAL DEVICES TO BIOLOGICAL SYSTEMS

(71) Applicant: UNIVERSITY HEALTH NETWORK, Toronto (CA)

(72) Inventors: Daniel Gavin Harrison, Toronto (CA); Geoffrey Samuel Frost, Toronto (CA); Thomas Kenneth Waddell, Toronto (CA); Laura Ann Wyvill, Mississauga (CA); Raymond Francis Cracauer, Beulah, CO (US); Shafique Keshavjee, Toronto (CA); Marcelo Cypel, Toronto (CA); Randy Yang, Oakville (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 449 days.

(21) Appl. No.: 15/302,751

(22) PCT Filed: Apr. 10, 2015

(86) PCT No.: PCT/CA2015/000240
§ 371 (c)(1),
(2) Date: Oct. 7, 2016

(87) PCT Pub. No.: WO2015/154170
PCT Pub. Date: Oct. 15, 2015

(65) Prior Publication Data
US 2017/0036006 A1    Feb. 9, 2017

Related U.S. Application Data

(60) Provisional application No. 61/977,978, filed on Apr. 10, 2014.

(51) Int. Cl.
*A61M 39/02* (2006.01)
*A01N 1/02* (2006.01)

(52) U.S. Cl.
CPC ....... *A61M 39/0247* (2013.01); *A01N 1/0247* (2013.01); *A61M 2039/0258* (2013.01);
(Continued)

(58) Field of Classification Search
CPC ........ A01N 1/0247; A61M 2039/0258; A61M 2039/0261; A61M 2039/0264;
(Continued)

(56) References Cited

U.S. PATENT DOCUMENTS 6,046,046 A * 4/2000 Hassanein ............ A01N 1/0247
435/284.1
6,459,917 B1 * 10/2002 Gowda .............. A61B 5/14528
600/345

(Continued)

FOREIGN PATENT DOCUMENTS

CN        1644156 A     7/2005
WO    WO-9300129 A1    1/1993

OTHER PUBLICATIONS

Harrison, Daniel Gavin et al., "Cannula for Connecting Medical Devices to Biological Systems", International Search Report dated Jun. 29, 2015.
(Continued)

*Primary Examiner* — Brandy S Lee
(74) *Attorney, Agent, or Firm* — Perry + Currier

(57) ABSTRACT

A cannula for connecting a medical device to a biological system is taught. The cannula includes a tissue engagement portion, preferably in the form of an annulus, to which a vacuum is applied through the cannula to attract and hold tissue of the biological system in an initial connection while an affixment device is applied to complete the connection. In addition to a working fluid conduit, comprising a main port, a working fluid passage and a working fluid port, and a port to apply the vacuum, the cannula can include a sensor port
(Continued)

to allow sensing pressure or other characteristics of the working fluid at a point closely adjacent to the connection between the cannula and the biological system.

19 Claims, 11 Drawing Sheets

(52) U.S. Cl.
CPC ............... *A61M 2039/0261* (2013.01); *A61M 2039/0264* (2013.01); *A61M 2039/0273* (2013.01); *A61M 2039/0276* (2013.01)

(58) Field of Classification Search
CPC .. A61M 2039/0273; A61M 2039/0276; A61M 39/0247; A61F 13/49; A61F 13/515; A61F 13/56
See application file for complete search history.

(56) References Cited

U.S. PATENT DOCUMENTS

| | | | |
|---|---|---|---|
| 6,537,290 B2 * | 3/2003 | Adams | A61B 17/00234 604/264 |
| 6,989,016 B2 | 1/2006 | Tallarida et al. | |
| 2002/0095067 A1 * | 7/2002 | Guenst | A61B 17/0206 600/37 |
| 2005/0255442 A1 * | 11/2005 | Brassil | A01N 1/02 435/1.2 |
| 2006/0212043 A1 * | 9/2006 | Grillo | A61B 17/3421 606/119 |
| 2013/0226288 A1 | 8/2013 | Goldwasser et al. | |
| 2013/0284181 A1 * | 10/2013 | Guerra | A61M 16/0463 128/207.14 |
| 2014/0088491 A1 | 3/2014 | Azarbarzin et al. | |

OTHER PUBLICATIONS

SIPO, First Office Action (with English translation), dated Jul. 26, 2018, re Chinese Patent Application No. 201580026977.3.
Extended European Search Report (EESR) dated Nov. 3, 2017, by EPO, re European Patent Application No. 15776037.2.
Written Opinion dated Jun. 29, 2015 for International Application No. PCT/CA2015/000240.
SIPO, Second Office Action (with English translation), dated Apr. 30, 2019, re Chinese Patent Application No. 201580026977.3.

* cited by examiner

CANNULA FOR CONNECTING MEDICAL DEVICES TO BIOLOGICAL SYSTEMS

FIELD OF THE INVENTION

The present invention relates to a cannula. More specifically, the present invention relates to a cannula for connecting a medical device to a biological system.

BACKGROUND OF THE INVENTION

Cannulae are well known and widely employed in the medical arts. Cannulae can be used to remove fluids from a biological system, such as removing blood from a vein or artery, or to introduce fluids into a biological system, such as providing saline, drugs, gases or other substances to a body.

In some cases, the cannula is merely a tube through which material may flow, but in other cases the cannula can be a more complex device allowing the affixing of the biological system to the cannula on a permanent or semi-permanent basis. Such affixing is performed to inhibit unintended disconnections of the biological system from the cannula due to movement of the biological system with respect to the cannula and/or due to pressure differences between a working fluid shared between the biological system and the medical device, etc.

To date, in all but the simplest cases (wherein the cannula may be retained in place via adhesive tape or similar techniques), affixing a cannula to a biological system has required surgical skills to be employed. Typically, the cannula is affixed to the biological system by a surgeon or medical technician who sutures the cannula to the biological system. Such procedures require the person performing them to have a high level of skill and often require long periods of time to perform the suturing, specialized equipment and/or a suitable environment to successfully perform the necessary joining.

In some cases, the biological system to which the cannula is to be attached can be especially challenging with which to achieve a desired connection. For example, in extracorporeal perfusion of lungs the pulmonary vein and/or a portion of the left atrium of the heart must be connected to a perfusion device via a cannula. Generally, the amount of the pulmonary vein or atrium available to be used to receive the stitches is quite limited and the pulmonary vein or atrium is exceedingly difficult to handle, being very slippery and with little, if any, rigidity. Thus, it takes a great deal of professional skill and time to suture a cannula to such biological systems.

It is desired to have a cannula which can be affixed to biological systems, including challenging biological systems such as pulmonary veins and/or heart atria, without requiring the levels of professional skill and time required for prior art cannulae. Further, it is desired to have such a cannula which can inhibit unintended disconnections of the cannula from the biological system due to relative movement there between or other factors.

SUMMARY OF THE INVENTION

It is an object of the present invention to provide a novel cannula for interfacing a medical device to a biological system which obviates or mitigates at least one disadvantage of the prior art.

According to a first aspect of the present invention, there is provided a cannula for connecting a medical device to a biological system comprising: a body having a first region and a second region, the first region including a main port for a working fluid and a vacuum port and the second region having a working fluid port in fluid communication with the main port and a tissue engagement portion, the tissue engagement portion comprising a groove about the exterior of the body and encircling the working fluid port, the groove including at least one vacuum outlet in fluid communication with the vacuum port.

Preferably, the groove includes a plurality of vacuum ports in fluid communication with the vacuum port. Also preferably, the second region further includes stand offs adjacent the working fluid port to inhibit direct contact between the working fluid port and a biological system to which the cannula is connected which might otherwise obstruct the flow of working fluid.

According to another aspect of the present invention, there is provided a cannula kit to connect a medical device to a biological system, the kit comprising: a body having a first region and a second region, the first region including a main port for a working fluid and a vacuum port and the second region having a working fluid port in fluid communication with the main port and a tissue engagement portion, the tissue engagement portion comprising a groove about the exterior of the body and encircling the working fluid port, the groove including at least one vacuum outlet in fluid communication with the vacuum port; and an affixment device to encircle tissue of a biological system at the tissue engagement portion and to maintain the tissue engaged therewith.

Preferably, the affixment device is a silk surgical suture, a resilient O-ring or a cable tie.

The present invention provides a novel cannula for connecting a medical device to a biological system. The cannula includes a tissue engagement portion, preferably in the form of an annulus, to which a vacuum is applied through the cannula to attract and hold tissue of the biological system in an initial connection while an affixment device is applied to complete the connection. The affixment device can be a wide variety of devices to establish a connection between the biological system and the cannula at the tissue engagement portion, including a silk surgical tie, a cable tie, a resilient member, such as a medical O-ring, etc. In addition to a working fluid conduit, comprising a main port, a working fluid passage and a working fluid port, and a port to apply the vacuum, the cannula can include a sensor port to allow sensing pressure or other characteristics of the working fluid at a point closely adjacent to the connection between the cannula and the biological system.

BRIEF DESCRIPTION OF THE DRAWINGS

Preferred embodiments of the present invention will now be described, by way of example only, with reference to the attached Figures, wherein.

DETAILED DESCRIPTION OF THE INVENTION

Figure 1:
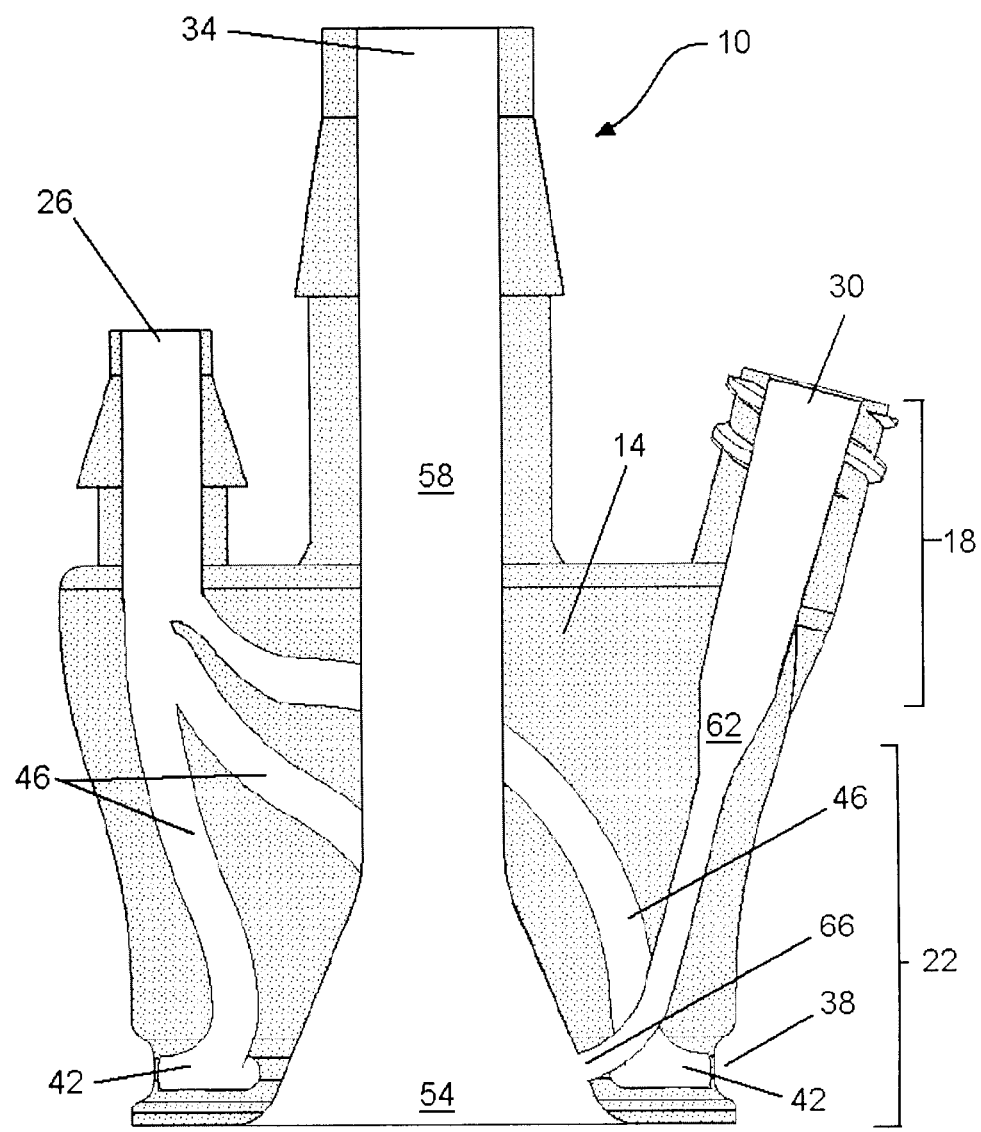
FIG. 1 shows a side cross section, taken through line A-A of FIG. 2, of a cannula in accordance with the present invention.
Figure 2:
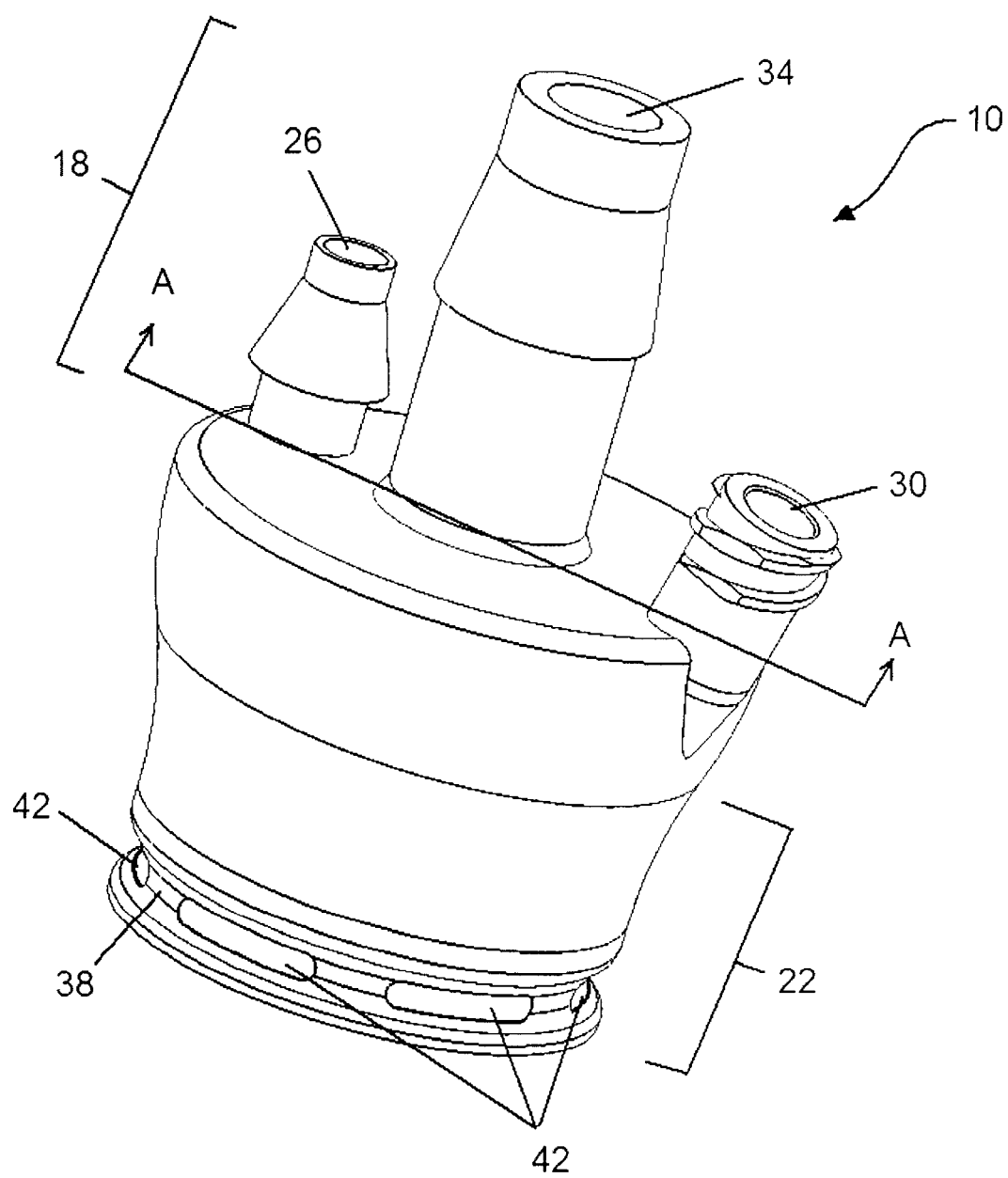
FIG. 2 shows a perspective view of a side and top of the cannula of FIG. 1.
Figure 3:
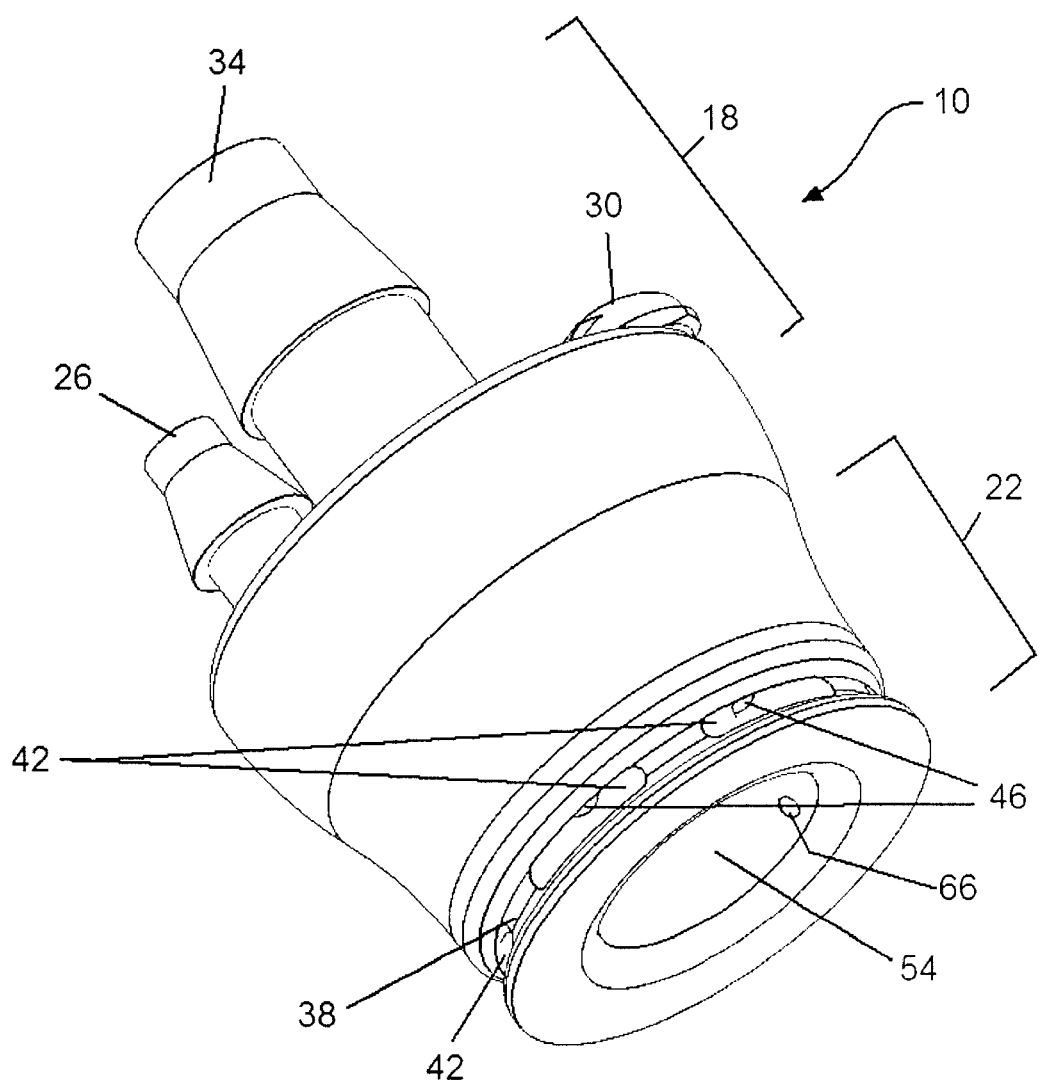
FIG. 3 shows a perspective view of a side and bottom of the cannula of FIG. 1.

A cannula in accordance with an embodiment of the present invention is indicated generally at 10 in FIG. 1. As described in more detail below, cannula 10 comprises a body 14 having a first region 18 comprising one or more ports for connecting to a medical device and a second region 22 for connection to a biological system.

Body 14 can be fabricated from a variety of materials, including any one of, or any combination of, engineering nylon or other plastic materials, stainless steel, aluminum, etc. and can be fabricated by injection molding, investment casting, 30 printing or via any number of other techniques as will be apparent to those of skill in the art. The primary limitations on the manufacture of body 14 are that it can be manufactured in a medically sterile manner, or that it can be suitably sterilized subsequent to manufacture. In a presently preferred embodiment, cannula 10 is manufactured by 3D printing from a suitable plastic material compliant with ISO 10993, for biocompatibility, and which is suitable for sterilization via Gamma or EtO sterilization processes and is a "single use" device which is disposed of after it has been used.

In the embodiment of FIGS. 1 through 4, cannula 10 includes three ports to which a medical device and/or device subsystems can be attached. Specifically, cannula 10 includes a vacuum port 26, a sensing port 30 and a main port 34.

Main port 34 serves as the working fluid (e.g. —perfusion fluid, blood, plasma, etc) connection of cannula 10 to the medical device. Vacuum port 26 allows a medical vacuum to be supplied to cannula 10, as described in more detail below, and sensing port 30 provides access for the sensing of the pressure and/or other characteristics of the working fluid moving through manifold port 34 into, or out of, the biological system to which cannula 10 is affixed. Such other characteristics can include temperature, pH, dissolved gasses, etc.

Second region 22 of cannula 10 includes a tissue engagement portion 38 which, in this embodiment, is an annular groove, or indented portion of reduced diameter relative to the adjacent portions of second region 22, formed in body 14. In other embodiments, tissue engagement portion 38 can include a textured or barbed surface instead of, or in addition to, the groove shown in the Figures. In still other embodiments, the groove and surface features (such as textures or barbs) can be omitted from tissue engagement portion 38. As shown in the Figures, tissue engagement portion 38 includes a plurality of vacuum outlets 42 each of which is in fluid communication with vacuum port 26 via vacuum passages 46 that are formed through body 14. In the illustrated embodiment, cannula 10 includes six vacuum outlets 42 but, as will be apparent to those of skill in the art, more or fewer vacuum outlets can be provided in cannula 10 as desired and/or required for specific applications.

Second region 22 further includes a working fluid port 54 which is connected to main port 34 by a working fluid passage 58. As can be seen in the Figures, tissue retention annulus 38 surrounds working fluid port 54. The combination of main port 34, working fluid passage 58 and working fluid port 54 forms a conduit allowing working fluid to be transferred between the medical device and the biological system through cannula 10. The conduit formed by main port 34, working fluid passage 58 and working fluid port 54 can include a chamber adjacent to working fluid port 54 that has a greater cross-sectional area (perpendicular to the direction of fluid flow) than the remainder of the conduit. An example of such a chamber is shown in FIG. 1, in the form of a conical expansion of the conduit approaching working fluid port 54. The chamber need not be conical in other embodiments.

Sensing port 30 is connected, via a sensing passage 62, to a sample port 66 which, preferably, is located immediately adjacent to working fluid port 54, to allow for the accurate sensing of the pressure, or other characteristics, of the working fluid as close to the connected biological system as possible.

While, in the illustrated embodiment, body 14 is shown as having a cylindrical shape, the present invention is not so limited and it is contemplated that other shapes can be employed to better complement some biological systems, if desired. For example, it is contemplated that body 14 can be fabricated with an oval or elliptical cross section presented to the biological system to be connected with, or with other shapes that may advantageously engage particular biological systems as will occur to those of skill in the art. Body 14 can have a variety of other cross-sectional shapes, including irregular shapes. In general, the shape of body 14 can be selected based on the shape of the biological system and medical devices to be connected by cannula 10.

It is also contemplated that body 14 can include a second working fluid port (not shown) which can be used as a sampling port to provide a small amount of working fluid to a technician, or sensor, for testing of various characteristics of interest, or to allow the introduction of drugs or other materials into the working fluid and connected biological system.

Figure 4:
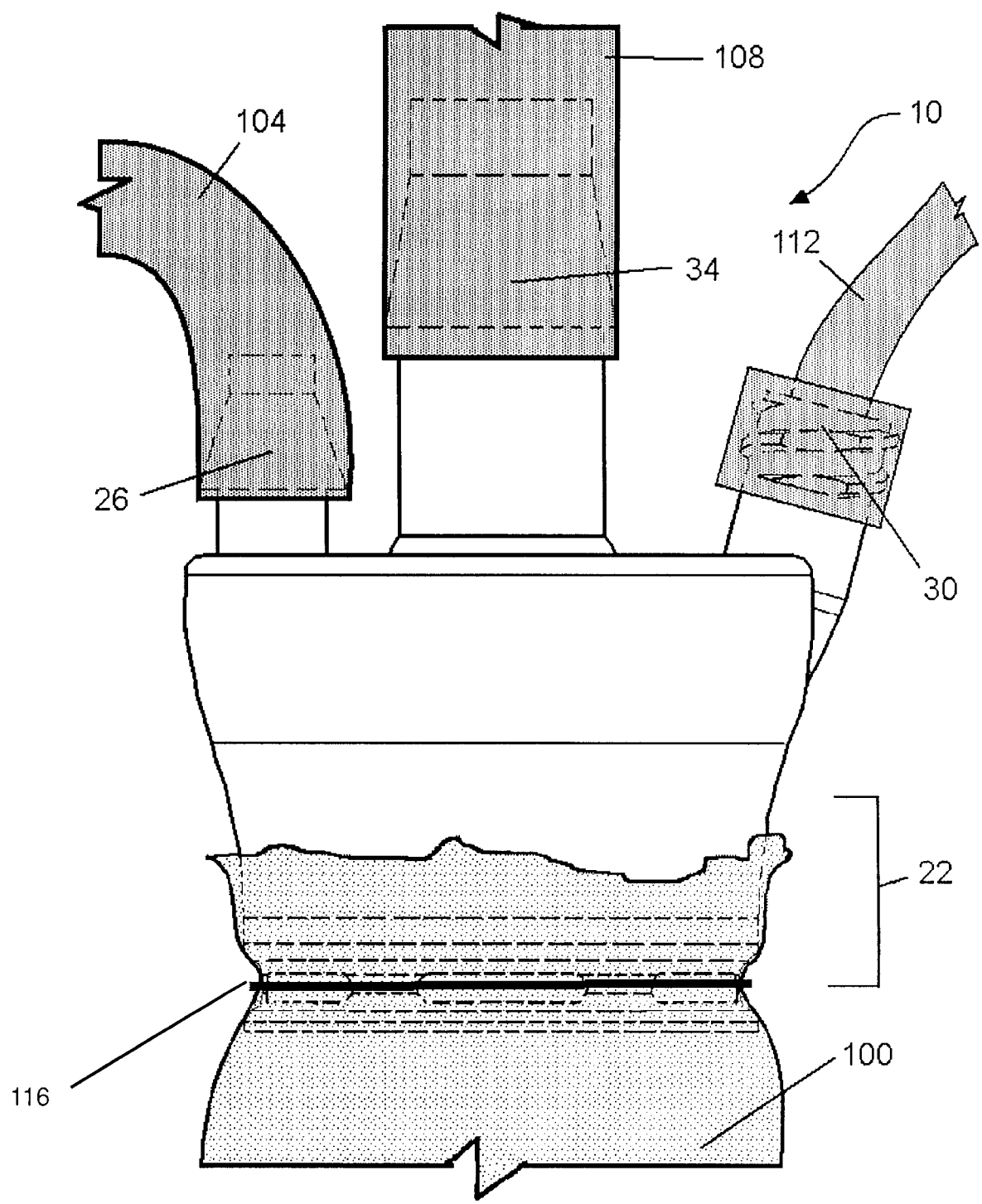
FIG. 4 shows a side view of the cannula of FIG. 1 which has been connected to a pulmonary vein.
Figure 10:
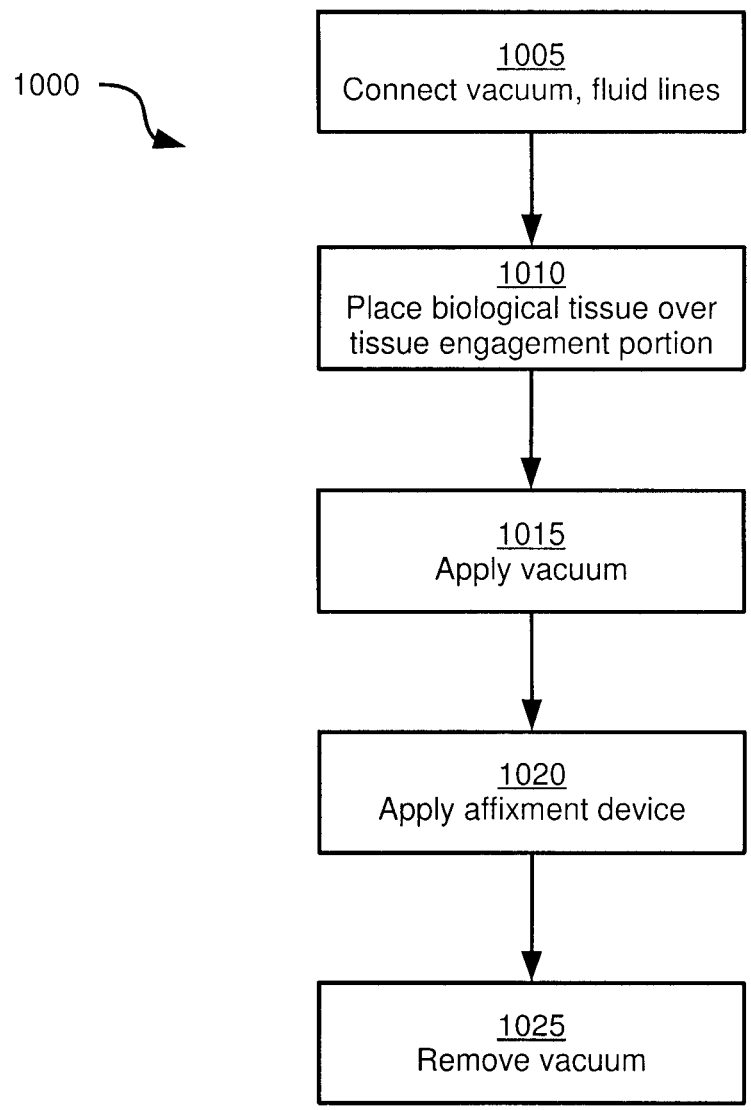
FIG. 10 shows a flowchart depicting a method of connecting the cannula of FIG. 1 to a biological system, in accordance with the present invention.

FIG. 4 shows a representative example of the connection of cannula 10 to a pulmonary vein 100 and to a vacuum supply 104, a working fluid reservoir 108 and a pressure sensor feedline 112. FIG. 10 depicts a method 1000 of connecting the cannula 10 to a pulmonary vein or other biological system, and will also be referred to in the discussion below.

To make the connection of FIG. 4 between the cannula 10 and the pulmonary vein 100, vacuum supply 104 is connected to vacuum port 26 at block 1005 of method 1000. At this point, working fluid reservoir 108 and/or pressure sensor feedline 112 can also be connected, or either or both of these can optionally be connected after the cannula 10 has been connected to the pulmonary vein 100. In the illustrated embodiment, the connection to sensing port 30 is shown as being a Luer connector, but any suitable means of making a connection can be employed as desired.

Following the connection of vacuum supply 104 to vacuum port 26, at block 1010 of method 1000, the operator, who will typically only need to be a medical technician with moderate skills, then draws the pulmonary vein 100 up over second region 22 (more specifically, over tissue engagement portion 38) until pulmonary vein tissue completely covers tissue engagement portion 38. With biological tissue covering each vacuum outlet 42 of tissue engagement portion 38, the performance of method 1000 proceeds to block 1015, at which a vacuum is applied to vacuum port 26 via vacuum supply 104 (that is, a vacuum pump or other apparatus connected to vacuum supply 104 is switched on). That vacuum is, in turn, applied to vacuum outlets 42 via vacuum passages 46. As will be apparent to those of skill in the art, as the tissue of pulmonary vein 100 overlies each vacuum outlet 42, the vacuum supplied to the respective outlet 42 will suction the pulmonary vein tissue onto tissue engagement portion 38 and will assist in maintaining the tissue in place, in an initial connection, until a final connection is made to affix the tissue as described below.

In many cases, the supplied vacuum will provide an added benefit in that the technician or other medical professional making the connection of cannula 10 to the pulmonary vein 100, or other biological system, will hear an audible noise caused by the vacuum drawing atmosphere through vacuum outlets 42. As biological tissue engages and obstructs each vacuum outlet 42, the volume of the audible noise will decrease correspondingly, until the noise terminates when the pulmonary, or other biological, tissue has engaged and obstructed all of vacuum outlets 42. When this happens, the medical technician will know that a good initial connection has been achieved. If the vacuum noise does not terminate, the technician will know that they have failed to make a good initial connection and to further manipulate pulmonary vein 100 until the noise terminates indicating that such a good initial connection has been obtained.

Once a good initial connection has been obtained, with some portion of the tissue of pulmonary vein, or other biological system, covering tissue engagement portion 38, at block 1020 of method 1000 an affixment device 116 can be employed by the operator to complete the connection. The affixment device 116 encircles the biological tissue engaging the tissue engagement portion 38 and is tightened to further compress the biological tissue into tissue engagement portion 38, thus completing the affixation of the biological tissue to cannula 10. Once the affixment device 116 is properly in place the supply of vacuum to vacuum port 26 can be removed, if desired (block 1025 of method 1000). Removal of the vacuum can be achieved by switching off the vacuum-generating apparatus (e.g. a vacuum pump) connected to vacuum supply 104, or by disconnecting vacuum supply 104 from vacuum port 26.

In some embodiments, if the vacuum is sufficiently strong, the application of affixment device 116 may be omitted. In other embodiments, the order of at least some of the above steps may be changed. For example, in some embodiments block 1015 (application of the vacuum) may be performed before block 1010 (placement of biological tissue over tissue engagement portion).

In the illustrated embodiment of FIG. 4, affixment device 116 is a silk surgical suture that is tied around tissue engagement portion 38. Affixment device 116 can also be nylon, cotton, or the like, or any suitable combination thereof. The proper use of such an affixment device is well within the skills of a medical technician, and is much less difficult to perform than the prior art technique of suturing the biological system to the cannula, which typically required advanced surgical skills.

It is also contemplated that a wide variety of other technologies can be employed as affixment device 116. For example, a resilient medical (sterile) O-ring can be employed instead of the silk surgical suture, the O-ring being stretched over the biological tissue and tissue engagement portion 38 and then released to compress the biological tissue in place in tissue engagement portion 38 to achieve the desired connection. As another example, a so-called "cable tie" can be employed as affixment device 116 and medical versions of such cable ties are commonly available. It is also contemplated that a second affixment device (not shown) can also be employed above (more distal from tissue engagement portion 38) tissue affixment device 116 to further secure the biological tissue if desired. In such a case, body 14 can include a second annular groove, or indented portion of reduced diameter (not shown) which the second affixment device can engage, but in such a case no vacuum outlets 42 would be provided in the second annular groove. In still further embodiments, a second annular groove as mentioned above can include a second set of vacuum outlets, also connected to vacuum port 26.

As should now be apparent to those of skill in the art, the actual selection and configuration of affixment device 116 is not particularly limited and a wide variety of solutions will occur to those of skill in the art.

While in the above-described embodiment tissue engagement portion 38 is in the form of an annulus (e.g. —a groove in the cylindrical body 14), the present invention is not so limited and tissue engagement portion 38 can be formed in a variety of other shapes, depending upon the biological system to which cannula 10 is to be attached and/or the cross sectional shape of body 14 presented to the biological system. For example, tissue engagement portion 38 can be formed as an ellipsoidal groove in body 14, etc. As mentioned earlier, a variety of other shapes, including irregular shapes, can be employed for tissue engagement portion 38.

Figure 5:
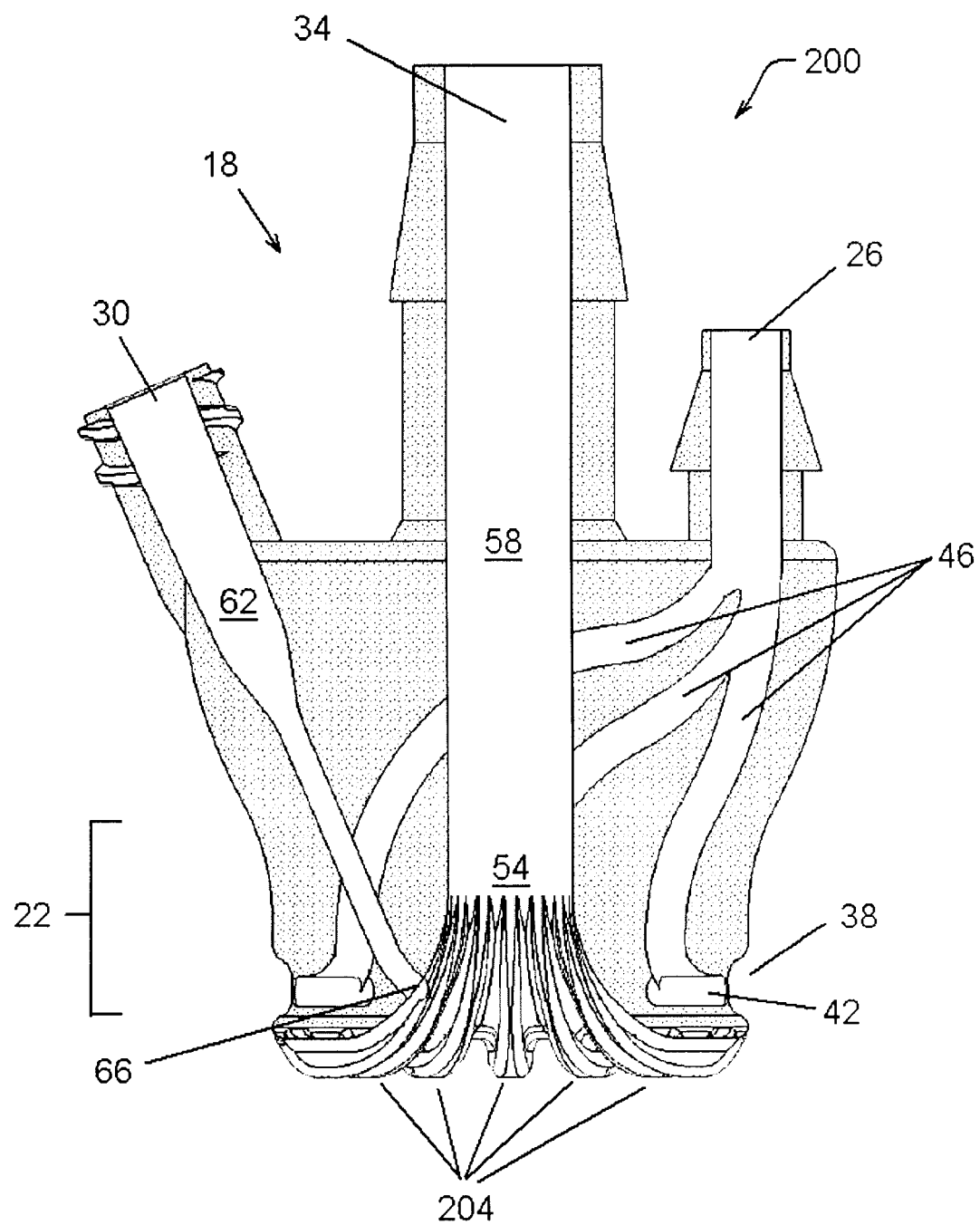
FIG. 5 shows a side cross section, taken through line B-B of FIG. 6, of another cannula in accordance with the present invention.
Figure 6:
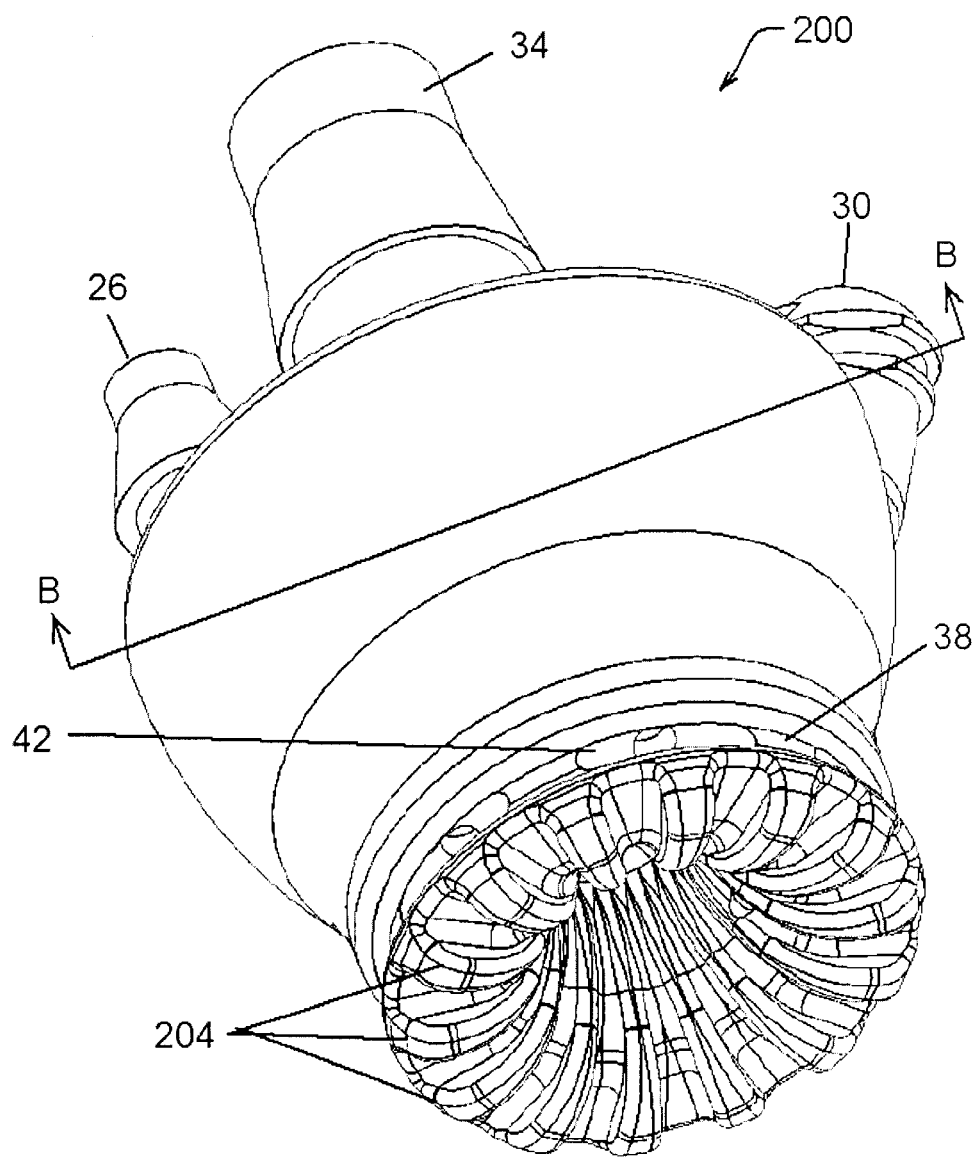
FIG. 6 shows a perspective view of the bottom and side of the cannula of FIG. 5.

FIGS. 5 and 6 show another embodiment of a cannula, indicated generally at 200, in accordance with the present invention and wherein like components to those of the embodiment of FIGS. 1-4 discussed above, are indicated with like reference numerals.

As best seen in FIG. 6, cannula 200 includes a set of stand offs in the form of upraised flutes 204 which operate to prevent the surface of cannula 200 surrounding working fluid port 54 from directly abutting the biological system to which cannula 200 is connected, to ensure that flow to and/or from working fluid port 54 is not restricted by such abutment.

While the illustrated embodiment includes flutes 204 which are formed with body 14, it is contemplated that similar stand offs can be provided instead by providing one or more metal or plastic protrusions or legs, or by employing loops of metal or plastic to form a cage-like structure adjacent working fluid port 54 to inhibit direct abutment of working fluid port 54 with the biological system to which cannula 200 is connected.

Figure 7:
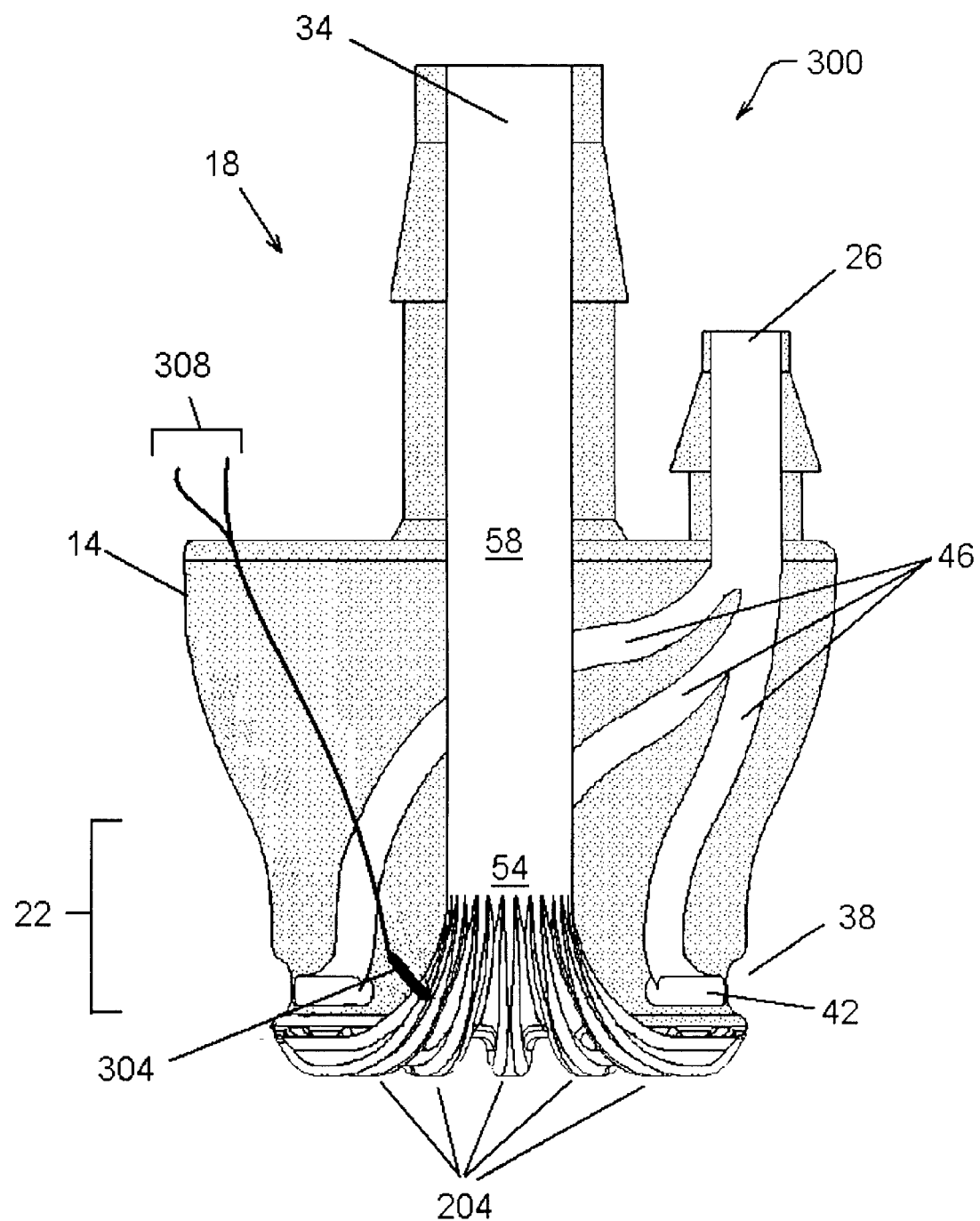
FIG. 7 shows a side cross section, taken from a similar viewpoint as that of FIG. 5, of another cannula in accordance with the present invention.

FIG. 7 shows another embodiment of a cannula, indicated generally at 300, in accordance with the present invention and wherein like components to those of the embodiment of FIGS. 5-6 discussed above, are indicated with like reference numerals. In this embodiment, a solid state sensor 304 is included in body 14 in place of sensing port 30, sensing passage 62 and sample port 66. Solid state sensor 304 can be used to sense one or more characteristics of the working fluid, such as pressure, temperature, pH, dissolved gasses content, etc. Solid state sensor 304 can also include an acoustic sensor to detect the absence or present of the above-mentioned vacuum noise, as used as an indicator of the desired initial connection.

With some manufacturing techniques for cannula 300, such as injection molding, or casting, solid state sensor 304 can be molded in place with its electrical leads 308 extending from region 18 of body 14, while with other manufacturing techniques solid state sensor 304 can be affixed, by a suitable epoxy, etc., in an appropriate aperture provided for it, and its electrical leads 308, in body 14. In other embodiments, solid state sensor 304 can be a wireless sensor (e.g. powered by a battery and including wireless data transmission hardware); in such embodiments, leads 308 can be omitted. It is also contemplated that in some circumstances, the need for a sensor may not exist and sensing port 30, and its associated sensing passage 62 and sample port 66 can be omitted altogether, as could solid state sensor 304.

While in the embodiments and examples discussed above working fluid port 54, working fluid passage 58 and main port 34 are arranged in a substantially straight configuration, it is contemplated that, in some circumstances, it may be desirable to have main port 34 at an angle to working fluid port 54. For example, main port 34 can be located at a ninety degree angle with respect to working fluid port 54 and such a geometry, and a variety of others, can be achieved by configuring the shape and/or position of working fluid passage 58 as desired. Similarly, vacuum port 26 and/or sensing port 30 (if present) can be located in a variety of different arrangements as may be desired to accommodate different physical needs of connecting to a variety of biological systems.

Figure 8:
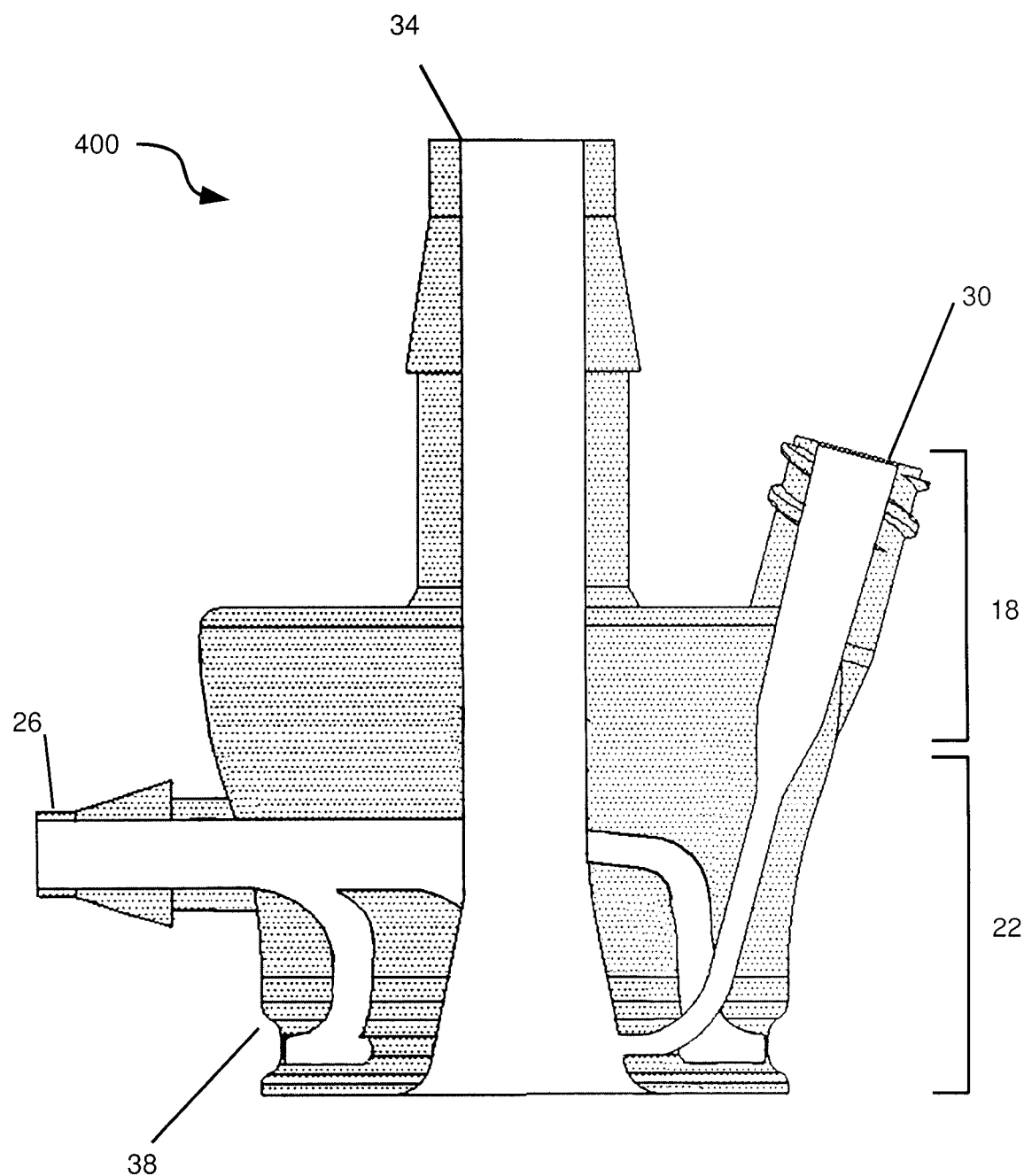
FIG. 8 shows a side cross section, taken from a similar viewpoint as that of FIG. 1, of a cannula in accordance with a further embodiment of the present invention.

In further embodiments, one or more of main port 34, vacuum port 26 and sensing port 30 need not be located in first region 18. Instead, as shown in FIG. 8, in a further embodiment of a cannula, indicated generally at 400, at least one of main port 34, vacuum port 26 and sensing port 30 can be located to second region 22. In particular, in the variation shown in FIG. 8, vacuum port 26 is located within second region 22. More generally, vacuum port 26, sensing port 30 and main port 34 may be located anywhere on cannula 10 that does not interfere with the placement of biological tissue over tissue engagement portion 38.

Figure 9:
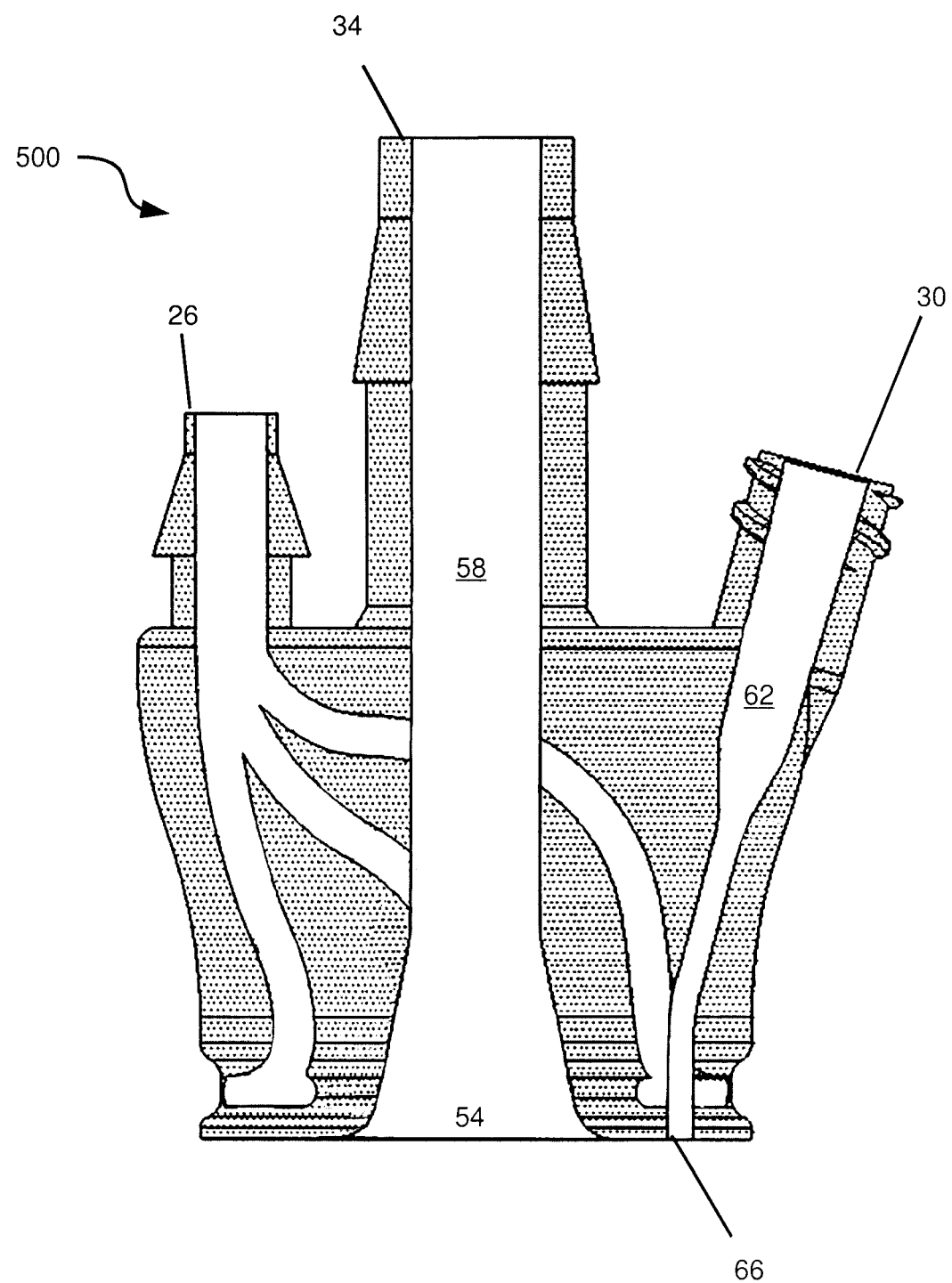
FIG. 9 shows a side cross section, taken from a similar viewpoint as that of FIG. 1, of a cannula in accordance with yet another embodiment of the present invention.

In still further embodiments of a cannula, as indicated generally at 500 in FIG. 9, sample port 66 need not be located within working fluid passage 58 adjacent to working fluid port 54. Instead, sample port 66 can be located adjacent to working fluid port 54 but outside working fluid passage 58.

Cannulae in accordance with the present invention have been found to be particularly useful for extra-corporeal organ perfusion systems and, in particular, for extra-corporeal lung perfusion. In prior art extra-corporeal perfusion systems, a skilled surgeon was required to suture the pulmonary vein to the perfusion system cannula and such an operation often took twenty minutes or more. With the cannulae of the present invention, a surgeon can achieve a desired connection between the cannula and the pulmonary vein in a few minutes and, in fact, such a connection can be achieved by a less skilled medical technician in about the same time. Further, the connection obtained with the present invention is robust and can easily survive transportation of the organ, such as from a donor harvesting location to a transplant location.

However, cannulae in accordance with the present invention are not limited to use for extra-corporeal organ perfusion and can alternatively be used in a wide variety of situations wherein it is desired to obtain a reliable affixment of a cannula to a biological system without requiring advanced surgical skills and/or an undue amount of time to achieve the affixment. For example, in some embodiments a cannula as described herein can be employed for accurate measurement of pressures across the tympanic membrane of an ear (e.g. a human ear), by connecting the working fluid port 54 to the irregular external geometry of the ear.

Figure 11:
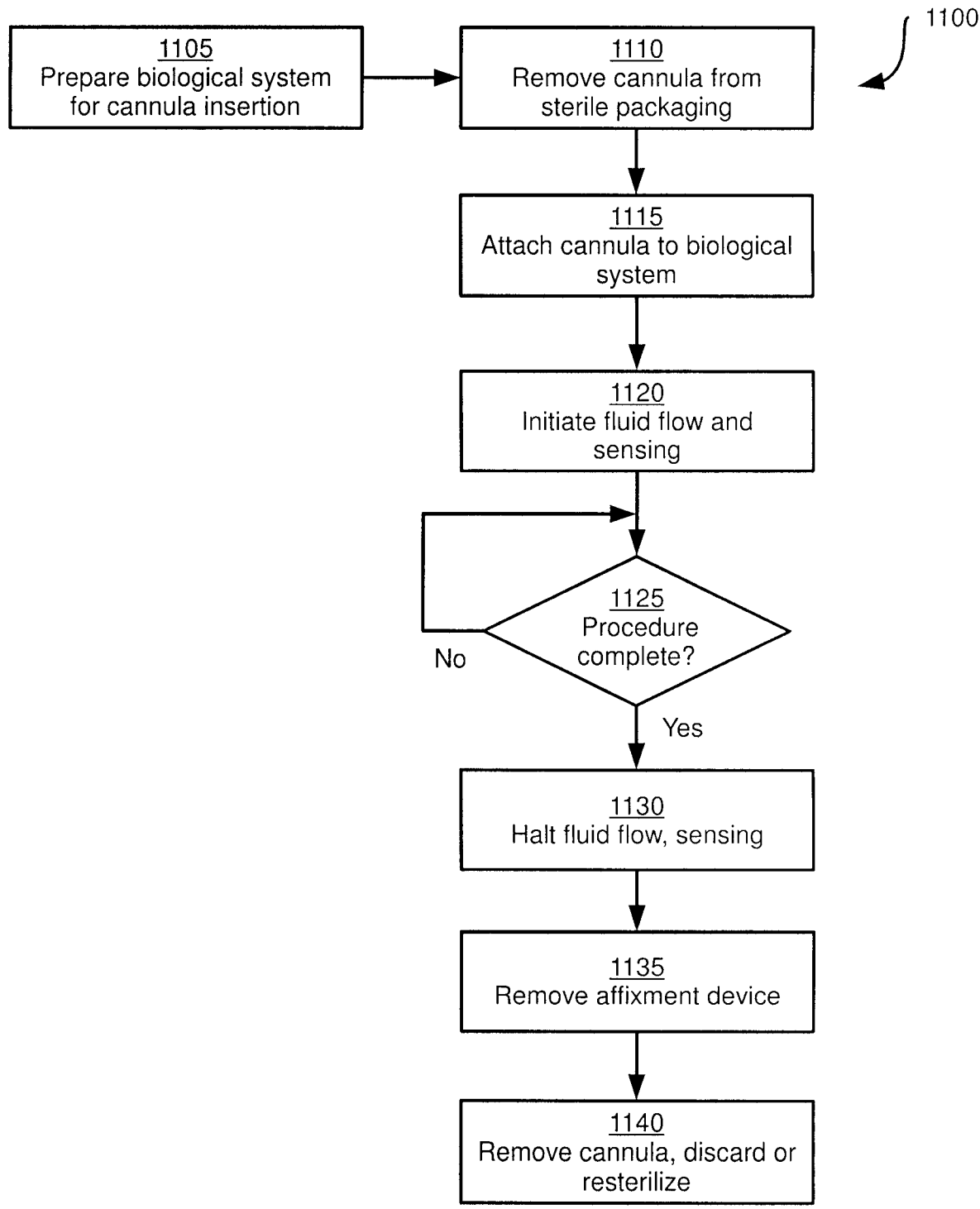
FIG. 11 shows a flowchart depicting a method of using the cannula of FIG. 1 with a biological system.

Referring now to FIG. 11, a method 1100 of using a cannula as described herein is illustrated. At block 1105, the biological system (e.g. a lung being readied for transplantation) is prepared for cannula insertion. Preparation of the biological system may include, for example, cleaning or other manipulation of the tissue to be connected to the cannula. At block 1110, the cannula (e.g. any of cannulae 10, 200, 300, 400 and 500 mentioned above, or any of the variations discussed herein) is removed from its sterile packaging. At block 1115, the cannula is attached to the prepared biological system, for example by performing method 1000.

Once the cannula is attached to the prepared biological system, at block 1120 fluid flow into the biological system is initiated via main port 34 and working fluid port 54. In some embodiments, where sensors are employed, sensing can also be initiated at block 1120, for example via sensing port 66 or sensor 304. At block 1125, fluid flow (and sensing, if employed) is continued until the procedure is complete. Completion can include any one of, or any combination of, the completion of a treatment of the biological system, the completion of transport of the biological system to a transplant location, and the like.

When the procedure is complete, the performance of method 1100 proceeds to block 1130. At block 1130, fluid flow to the biological system via the cannula is halted. If sensing was initiated at block 1120, such sensing is also halted at block 1130. At block 1135, the affixment device attaching the cannula to the biological system is removed. At block 1140, the cannula is disconnected from the biological system. The cannula can then be discarded, or resterilized for further use.

The present invention provides a novel cannula for connecting a medical device to a biological system. The cannula includes a tissue engagement portion, preferably in the form of an annulus, to which a vacuum is applied through the cannula to attract and hold tissue of the biological system in an initial connection while an affixment device is applied to complete the connection. The affixment device can be a wide variety of devices to establish a connection between the biological system and the cannula at the tissue engagement portion, including a silk surgical tie, a cable tie, a resilient member, such as a medical O-ring, etc. In addition to a working fluid conduit, comprising a main port, a working fluid passage and a working fluid port, and a port to apply the vacuum, the cannula can include a sensor port to allow sensing pressure or other characteristics of the working fluid at a point closely adjacent to the connection between the cannula and the biological system.

The above-described embodiments of the invention are intended to be examples of the present invention and alterations and modifications may be effected thereto by those of skill in the art without departing from the scope of the invention which is defined solely by the claims appended hereto.

We claim:

1. A cannula for connecting a medical device to a biological system, comprising:
   a body including a main port for a working fluid, a working fluid port, and at least one sidewall between the main port and the working fluid port, the at least one sidewall defining a conduit extending through the body between the working fluid port and the main port, the conduit configured to transfer the working fluid between the main port and the biological system, via the working fluid port;

the body further including a tissue engagement portion having an annular groove encircling the working fluid port on the at least one sidewall between the main port and the working fluid port; and the body further including a vacuum port, at least one vacuum outlet at the annular groove of the tissue engagement portion, and at least one vacuum passage extending through the body between the at least one vacuum outlet and the vacuum port.

2. The cannula of claim 1 wherein the at least one vacuum outlet includes a plurality of vacuum outlets at the annular groove, in fluid communication with the vacuum port via a plurality of vacuum passages.

3. The cannula of claim 1, the body further including a sensing port, a sample port adjacent the working fluid port, and a sensing passage extending through the body between the sensing port and the sample port.

4. The cannula of claim 1, further comprising a solid state sensor located adjacent the working fluid port.

5. The cannula of claim 4 wherein the solid state sensor is a pressure sensor.

6. The cannula of claim 1, the body further including stand offs adjacent the working fluid port to inhibit direct contact between the working fluid port and a biological system to which the cannula is connected.

7. The cannula of claim 6 wherein the stand offs are in the form of upstanding flutes.

8. The cannula of claim 6 wherein the stand offs are in the form of a cage about the working fluid port.

9. The cannula of claim 1 wherein the cross section of the body presented to the biological system is circular.

10. The cannula of claim 1 wherein the cross section of the body presented to the biological system is one of ellipsoidal and irregular.

11. The cannula of claim 1 wherein the body is formed by injection molding.

12. The cannula of claim 1 wherein the body is formed by 3D printing.

13. The cannula of claim 1, the conduit including a chamber adjacent to the working fluid port.

14. The cannula of claim 13, wherein the chamber is conical.

15. A method of connecting a cannula according to claim 1 to a biological system, comprising:

inserting the working fluid port into the biological system to place biological tissue over the at least one vacuum outlet of the tissue engagement portion;

applying a vacuum to the vacuum port;

applying an affixment device about the tissue engagement portion to affix the biological tissue to the tissue engagement portion; and removing the vacuum from the vacuum port.

16. A cannula kit to connect a medical device to a biological system, the kit comprising:

a cannula having:

a body including a main port for a working fluid, a working fluid port, and at least one sidewall between the main port and the working fluid port, the at least one sidewall defining a conduit extending through the body between the working fluid port and the main port, the conduit configured to transfer the working fluid between the main port and the biological system, via the working fluid port;

the body further including a tissue engagement portion having an annular groove encircling the working fluid port on the at least one sidewall between the main port and the working fluid port;

the body further including a vacuum port, at least one vacuum outlet at the annular groove of the tissue engagement portion, and at least one vacuum passage extending through the body between the at least one vacuum outlet and the vacuum port; and an affixment device to encircle tissue of a biological system at the tissue engagement portion and to maintain the tissue engaged therewith.

17. The kit of claim 16 wherein the affixment device is a surgical suture.

18. The kit of claim 16 wherein the affixment device is a resilient O-ring.

19. The kit of claim 16 wherein the affixment device is a cable tie.

* * * * *